(12) United States Patent
Weber (10) Patent No.: US 7,736,350 B2
(45) Date of Patent: Jun. 15, 2010

(54) ABSORBENT ARTICLE WITH IMPROVED CONTAINMENT FLAPS

(75) Inventor: Shirlee A. Weber, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 576 days.

(21) Appl. No.: 10/334,028

(22) Filed: Dec. 30, 2002

(65) Prior Publication Data

US 2004/0127882 A1 Jul. 1, 2004

(51) Int. Cl.
*A61F 13/15* (2006.01)
*A61F 13/20* (2006.01)

(52) U.S. Cl. .......................... 604/385.27; 604/385.26; 604/385.28

(58) Field of Classification Search .................. 604/385, 604/396, 385.24–385.28, 386, 393, 394
See application file for complete search history.

(56) References Cited

U.S. PATENT DOCUMENTS

| | | | |
|---|---|---|---|
| D132,937 S | 6/1942 | Cadgene | |
| 2,538,596 A | 1/1951 | Sheridan | |
| 3,039,466 A | 6/1962 | Wilson | |
| 3,338,992 A | 8/1967 | Kinney | |
| 3,341,394 A | 9/1967 | Kinney | |
| 3,424,162 A | 1/1969 | Parravicini | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,855,046 A | 12/1974 | Hansen et al. | |
| 4,100,324 A | 7/1978 | Anderson et al. | |
| 4,205,679 A | 6/1980 | Repke et al. | |
| 4,227,531 A | 10/1980 | McLeod | |

(Continued)

FOREIGN PATENT DOCUMENTS

EP 0516877 * 12/1992

(Continued)

OTHER PUBLICATIONS

PAJ machine translation of entire specification for JP 05-031135 A.*

(Continued)

*Primary Examiner*—Melanie J Hand
(74) *Attorney, Agent, or Firm*—Dority & Manning, P.A.

(57) ABSTRACT

A pant-like absorbent article includes laterally extending front and back ear portions defined at opposed lateral sides of the front and back waist regions. A laterally inwardly directed leg contour is defined in each of the lateral sides between the respective front and back ear portions. An absorbent body structure extends between the front and back waist regions and includes laterally extending wing portions along the front and back ear portions. Leak guards are provided having a free laterally inward side and a laterally outward side with a contour corresponding generally to that of the article lateral sides and leg contours. The laterally outward sides of the guards are attached to the lateral sides of the front and back ear portions and along the leg contours laterally outward of the absorbent body structure so as to define a containment pocket along the leg contours and front and back ear portions.

21 Claims, 3 Drawing Sheets

U.S. PATENT DOCUMENTS

| | | | |
|---|---|---|---|
| 4,302,853 A | 12/1981 | Mesek | |
| 4,340,563 A | 7/1982 | Appel et al. | |
| 4,351,340 A | 9/1982 | McLeod | |
| 4,374,888 A | 2/1983 | Bornslaeger | |
| 4,375,448 A | 3/1983 | Appel et al. | |
| 4,402,690 A | 9/1983 | Redfern | |
| 4,427,408 A | 1/1984 | Karami et al. | |
| 4,486,192 A | 12/1984 | Sigl | |
| 4,490,148 A | 12/1984 | Beckerstrum | |
| 4,494,278 A | 1/1985 | Kroyer et al. | |
| 4,522,624 A | 6/1985 | Bolick | |
| 4,522,874 A | 6/1985 | Pommez | |
| D281,540 S | 12/1985 | Ternstrom | |
| 4,568,342 A | 2/1986 | Davis | |
| 4,581,772 A | 4/1986 | Smith | |
| 4,610,680 A | 9/1986 | LaFleur | |
| 4,610,681 A | 9/1986 | Strohbeen et al. | |
| 4,619,649 A | 10/1986 | Roberts | |
| 4,630,320 A | 12/1986 | Van Gompel | |
| 4,639,949 A | 2/1987 | Ales et al. | |
| 4,640,810 A | 2/1987 | Laursen et al. | |
| 4,641,381 A | 2/1987 | Heran et al. | |
| 4,646,362 A * | 3/1987 | Heran et al. | 2/400 |
| 4,655,760 A | 4/1987 | Morman et al. | |
| 4,657,802 A | 4/1987 | Morman | |
| 4,681,581 A | 7/1987 | Coates | |
| 4,695,278 A | 9/1987 | Lawson | |
| 4,704,115 A | 11/1987 | Buell | |
| 4,704,116 A | 11/1987 | Enloe | |
| 4,704,117 A | 11/1987 | Mitchell | |
| 4,720,415 A | 1/1988 | Vander Wielen et al. | |
| 4,738,677 A | 4/1988 | Foreman | |
| 4,743,246 A | 5/1988 | Lawson | |
| 4,753,646 A | 6/1988 | Enloe | |
| 4,762,521 A | 8/1988 | Roessler et al. | |
| 4,781,966 A | 11/1988 | Taylor | |
| 4,795,452 A | 1/1989 | Blaney et al. | |
| 4,795,454 A | 1/1989 | Dragoo | |
| 4,808,178 A | 2/1989 | Aziz et al. | |
| 4,822,435 A | 4/1989 | Igaue et al. | |
| 4,834,740 A | 5/1989 | Suzuki et al. | |
| RE33,106 E | 11/1989 | Beckestrom | |
| 4,880,423 A | 11/1989 | Green | |
| 4,897,084 A | 1/1990 | Ternstrom et al. | |
| 4,904,251 A | 2/1990 | Igaue et al. | |
| 4,909,803 A | 3/1990 | Aziz et al. | |
| 4,940,464 A | 7/1990 | Van Gompel et al. | |
| 4,944,733 A | 7/1990 | Casale | |
| 4,965,122 A | 10/1990 | Morman | |
| 4,978,345 A | 12/1990 | Holliday et al. | |
| 4,981,747 A | 1/1991 | Morman | |
| 4,995,873 A | 2/1991 | Knight | |
| D318,732 S | 7/1991 | Chautin | |
| 5,032,120 A | 7/1991 | Freeland et al. | |
| 5,057,368 A | 10/1991 | Largman et al. | |
| 5,069,970 A | 12/1991 | Largman et al. | |
| 5,087,255 A | 2/1992 | Sims | |
| D332,659 S | 1/1993 | Bisaga | |
| 5,226,992 A | 7/1993 | Morman | |
| D339,633 S | 9/1993 | Porter | |
| 5,246,433 A | 9/1993 | Hasse et al. | |
| D342,786 S | 12/1993 | De Gooijer | |
| 5,277,976 A | 1/1994 | Hogle et al. | |
| 5,284,703 A | 2/1994 | Everhart et al. | |
| D345,015 S | 3/1994 | Booth | |
| D346,214 S | 4/1994 | Bradford | |
| 5,336,545 A | 8/1994 | Morman | |
| 5,350,624 A | 9/1994 | Georger et al. | |
| 5,358,500 A * | 10/1994 | Lavon et al. | 604/385.29 |
| D354,130 S | 1/1995 | Johnson | |
| 5,382,246 A | 1/1995 | Kawano | |
| 5,385,775 A | 1/1995 | Wright | |
| RE34,920 E | 4/1995 | Aziz et al. | |
| 5,403,301 A | 4/1995 | Huffman et al. | |
| 5,464,401 A | 11/1995 | Hasse et al. | |
| 5,464,402 A | 11/1995 | Zajaczkowski | |
| 5,466,410 A | 11/1995 | Hills | |
| 5,486,166 A | 1/1996 | Bishop et al. | |
| 5,490,846 A | 2/1996 | Ellis et al. | |
| 5,527,171 A | 6/1996 | Soerensen | |
| 5,527,302 A * | 6/1996 | Endres et al. | 604/385.21 |
| 5,527,304 A | 6/1996 | Buell et al. | |
| H1558 H * | 7/1996 | Goulait et al. | |
| 5,558,659 A | 9/1996 | Sherrod et al. | |
| 5,567,265 A | 10/1996 | Zajaczkowski | |
| 5,575,783 A * | 11/1996 | Clear et al. | 604/385.22 |
| 5,575,874 A | 11/1996 | Griesbach, III et al. | |
| 5,591,152 A | 1/1997 | Buell et al. | |
| 5,601,547 A | 2/1997 | Kato et al. | |
| 5,624,425 A | 4/1997 | Gray et al. | |
| 5,645,542 A | 7/1997 | Anjur et al. | |
| 5,653,704 A | 8/1997 | Buell et al. | |
| D383,207 S | 9/1997 | Cassell | |
| 5,662,638 A | 9/1997 | Johnson et al. | |
| 5,674,216 A | 10/1997 | Buell et al. | |
| 5,676,661 A | 10/1997 | Faulks et al. | |
| 5,695,849 A | 12/1997 | Shawver et al. | |
| 5,707,364 A | 1/1998 | Coates | |
| 5,711,832 A | 1/1998 | Glaug et al. | |
| 5,746,732 A | 5/1998 | Olsson et al. | |
| 5,776,122 A | 7/1998 | Faulks et al. | |
| 5,801,107 A | 9/1998 | Everhart et al. | |
| 5,814,037 A | 9/1998 | Coates | |
| 5,899,894 A | 5/1999 | Palumbo et al. | |
| 5,938,652 A | 8/1999 | Sauer | |
| 5,952,252 A | 9/1999 | Shawver et al. | |
| 5,957,908 A | 9/1999 | Kline et al. | |
| 5,964,743 A | 10/1999 | Abuto et al. | |
| 5,993,433 A * | 11/1999 | St. Louis et al. | 604/385.27 |
| 6,102,892 A | 8/2000 | Putzer et al. | |
| 6,120,487 A | 9/2000 | Ashton | |
| 6,121,510 A | 9/2000 | Sauer | |
| 6,231,557 B1 | 5/2001 | Krautkramer et al. | |
| 6,314,627 B1 | 11/2001 | Ngai | |
| 6,336,921 B1 | 1/2002 | Kato et al. | |
| 6,358,350 B1 | 3/2002 | Glaug et al. | |
| 6,362,389 B1 | 3/2002 | McDowall et al. | |
| 6,375,889 B1 | 4/2002 | Holmes et al. | |
| 6,441,268 B1 | 8/2002 | Edwardsson | |
| 6,652,504 B1 * | 11/2003 | Olson et al. | 604/385.25 |
| 6,680,423 B1 * | 1/2004 | Tanzer | 604/380 |
| 6,682,512 B2 * | 1/2004 | Uitenbroek et al. | 604/385.16 |
| 6,682,514 B1 * | 1/2004 | Brunner | 604/385.24 |
| 6,716,205 B2 * | 4/2004 | Popp et al. | 604/385.24 |
| 6,830,566 B2 * | 12/2004 | Kuen et al. | 604/396 |
| 2001/0008180 A1 | 7/2001 | Anderson et al. | |
| 2001/0037850 A1 | 11/2001 | Marmon et al. | |
| 2002/0034907 A1 | 3/2002 | Groitzsch et al. | |
| 2002/0052591 A1 | 5/2002 | Zehner et al. | |
| 2002/0099347 A1 | 7/2002 | Chen et al. | |
| 2002/0104608 A1 | 8/2002 | Welch et al. | |
| 2006/0264858 A1* | 11/2006 | Roe et al. | 604/361 |

FOREIGN PATENT DOCUMENTS

| | | | |
|---|---|---|---|
| EP | 0627905 | * | 12/1994 |
| EP | 0662812 | * | 7/1995 |
| EP | 0670154 A2 | | 9/1995 |
| EP | 069231 A1 | | 1/1996 |
| EP | 0567792 | | 1/1998 |
| EP | 0734240 | * | 6/1998 |
| EP | 0701426 | * | 11/1998 |
| EP | 0701424 | * | 1/1999 |
| EP | 0992338 A2 | | 4/2000 |

| | | | |
|---|---|---|---|
| EP | 0872206 B1 | | 7/2000 |
| EP | 1050612 A1 | | 11/2000 |
| EP | 1080708 | * | 3/2001 |
| GB | 2270247 A | * | 3/1994 |
| GB | 2270247 A | | 3/1994 |
| JP | 9253123 | | 9/1997 |
| JP | 9253124 | | 9/1997 |
| JP | 10071173 | | 3/1998 |
| JP | 11347065 | | 12/1999 |
| JP | 2000316903 | | 11/2000 |
| JP | 2002200105 | | 7/2002 |
| JP | 2003199785 | | 7/2003 |
| WO | 9612615 | | 5/1996 |
| WO | 9822058 | | 5/1998 |
| WO | 9835642 | * | 8/1998 |
| WO | 9837841 | * | 9/1998 |
| WO | 9837842 | * | 9/1998 |
| WO | 9837843 | * | 9/1998 |
| WO | 9837844 | * | 9/1998 |
| WO | 9838956 | * | 9/1998 |
| WO | 9920821 | | 4/1999 |
| WO | 9923983 | * | 5/1999 |
| WO | 9948681 | * | 9/1999 |
| WO | 9953878 | * | 10/1999 |
| WO | 9960966 | * | 12/1999 |
| WO | 9960967 | * | 12/1999 |
| WO | 9960968 | * | 12/1999 |
| WO | 9960969 | * | 12/1999 |
| WO | 9960970 | * | 12/1999 |
| WO | 9960971 | * | 12/1999 |
| WO | 9960972 | * | 12/1999 |
| WO | 9960974 | * | 12/1999 |
| WO | 0008245 | | 2/2000 |
| WO | 0019950 | * | 4/2000 |
| WO | 00/37009 | | 6/2000 |
| WO | 0031331 | | 6/2000 |
| WO | 0035395 | * | 6/2000 |
| WO | WO 0031331 A1 | * | 6/2000 |
| WO | WO 0037016 A1 | * | 6/2000 |
| WO | WO 02/34184 A1 | | 5/2002 |

OTHER PUBLICATIONS

English translation of JP 05-031135 A, Abstract and paras.0021-0023, drawings.*
Patent Abstract of Japan No. 05-031135, Feb. 9, 1993 (With Translation).
Patent Abstract of Japan No. 09-313527, Dec. 9, 1997 (With Translation).
PCT Search Report, Feb. 26, 2004.

* cited by examiner

ABSORBENT ARTICLE WITH IMPROVED CONTAINMENT FLAPS

TECHNICAL FIELD OF THE INVENTION

The present invention relates generally to the field of absorbent articles and garments, such as disposable diapers, child's training pants, incontinence articles, and the like, which incorporate containment flaps along their side edges.

BACKGROUND

Many types of consumer products such as disposable diapers, training pants, feminine care articles, incontinence articles, and the like, utilize an absorbent pad structure for absorbing and wicking away bodily fluids. The absorbent pads are conventionally formed from an absorbent web, typically a non-woven fibrous web material formed by known techniques and are disposed between a liquid pervious topsheet and a liquid impermeable backsheet. Such absorbent articles may also include an elasticized waistband and leg cuffs to help reduce the leakage of body exudates. Some conventional absorbent articles have also included elasticized containment or barrier flaps at the leg or waist sections of the article to further reduce the occurrence of leaks.

Conventional pant-like absorbent structures, such as a child's training pant, have also incorporated containment flaps alongside of the absorbent structure. Reference is made, for example, to the HUGGIES® PULL-UPS® disposable training pants from Kimberly-Clark Corporation of Neenah, Wis. The use of containment flaps in training pants is also described, for example, in WO 00/35395 and U.S. Pat. No. 6,231,557 B1. With typical training pant configurations, the containment flaps are disposed relatively close to the longitudinal sides of a generally rectangular shaped absorbent body and serve as a barrier to any fluids that may leak from the sides of the absorbent body.

Conventional training pants may also include elastomeric side panels that are joined at side seams extending between a waist opening and respective leg openings. The seams may be permanent wherein the article is pulled onto the wearer in a manner similar to underwear. Alternatively, the seams may be releasable wherein the article may be put on and/or taken off similar to a disposable diaper. The containment flaps extend longitudinally along a central portion of the article on each side of the absorbent body from the waist to the back. However, with this type of configuration, it is not uncommon for leakage to occur at the sides of the article, particularly when fluid wicks around the edges of the article. This problem may be more likely when the wearer is lying down, particularly on their side. With conventional articles, the absorbent body does not extend across the abdomen and buttocks and the containment flaps are insufficient to prevent leakage around the upper and back sides of the absorbent body.

The present invention provides an improved absorbent body and containment flap configuration that will help minimize the occurrence of side area leaks, particularly in training pant articles.

SUMMARY OF THE INVENTION

Objects and advantages of the invention will be set forth in part in the following description, or may be obvious from the description, or may be learned through practice of the invention.

In general, the present invention provides an improved absorbent article that protects against leakage around the upper and back sides of the article. A particularly useful embodiment of the invention is a child's training pant. However, other absorbent articles such as incontinence devices, disposable diapers, and the like, are also within the scope and spirit of the invention.

A pant-like absorbent article includes a chassis defining a front waist region at a first longitudinal end, a back waist region at an opposite longitudinal end, and a crotch region extending longitudinally between said front and back waist regions. The chassis may be defined generally entirely of elastomeric materials, or may only have particular regions or portions made up of elastomeric materials. It should be appreciated that the materials used for the article are not a limiting factor, and that any combination of known materials and compositions made be used in the manufacture of articles according to the invention.

In a typical training pant configuration, laterally extending ear portions are defined at opposed lateral sides of one or both of the front and back waist regions. These ear portions extend around the front and back waist of a wearer and meet at side seams of the article. The ear portions also define laterally inwardly directed leg contours. When the chassis is formed into the pant-like article, the ear portions are joined at the side seams and the leg contours define leg openings in conjunction with the crotch region of the article.

An absorbent body structure has a central portion that extends longitudinally along said crotch region generally from the front waist region to the back waist region. The absorbent body structure includes laterally extending wing portions that extend laterally along the front and/or back ear portions of the chassis. The absorbent body structure may include any combination of conventional absorbent materials used in absorbent articles. In one embodiment, the absorbent body structure may be generally elastomeric, and in another embodiment the structure may be generally non-elastomeric.

Longitudinally extending leak guards or containment flaps are provided on the body-facing side of the chassis. Each guard has a free laterally inward side that, in certain embodiments, may be elasticized. Each guard has a laterally outward side with a contour corresponding generally to that of the crotch region and leg contours defined by the front and back ear portions. This laterally outward side of the guards may be attached to the chassis generally adjacent to the laterally outward sides of the chassis such that the leak guards define a containment pocket along the leg contours and at the front and back ear portions of the chassis. In this manner, upon folding the chassis about a transverse fold line at a longitudinal midpoint thereof to form a pant structure, the lateral sides of the front and back ear portions join at side seams of the article such that the leg contours define respective leg openings, and the absorbent body structure and leak guards extend laterally across the abdomen and across the back of a wearer between the side seams.

In a useful embodiment, at least the front and back ear portions of the chassis waist regions, including the absorbent article structure, are stretchable. For example, essentially the entire chassis may be stretchable. The leak guards are configured so as to be stretchable with at least the ear portions. For example, the guards may be made of an elastomerically stretchable material. In an alternate embodiment, the guards may be made of a non-elastomeric material, but may be gathered at the point of attachment with the ear portions so as to stretch therewith.

The absorbent article may include various types of side seam configurations. For example, the ear portions may be bonded at the side seams such that the wearer must pull the article on much like underwear. These bonded seams may also be tearable such that the article may be removed from the wearer by separating or tearing the seams and removing the article much like a diaper. In an alternate embodiment, the side seams are releasable and re-attachable. For example, a hook-and-loop or other type of re-attachable system may be used along the side seams.

Aspects of the invention will be described below in greater detail with reference to embodiments shown in the figures.

DETAILED DESCRIPTION

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

Within the context of the present description, the following terms may have the following meanings:

"Attached" refers to the bonding, joining, adhering, connecting, attaching, or the like, of two elements. Two elements will be considered to be attached together when they are bonded directly to one another or indirectly to one another, such as when each is directly attached to an intermediate element.

"Elastomeric" refers to a material or composite which can be stretched or elongated by at least 25% of its relaxed length and which will recover, upon release of the applied force, at least 10% of its elongation. It is generally preferred that the elastomeric material or composite be capable of being elongated by at least 100%, more preferably by at least 300%, of it relaxed length and recover at least 50% of its elongation. An elastomeric material is thus stretchable and "stretchable" and "elastomeric" may be used interchangeably.

"Elastic" or "Elasticized" means that property of a material or composite by virtue of which it tends to recover to almost its original size and shape after removal of a force causing a deformation.

"Neck-bonded" laminate refers to a composite material having an elastic member that is bonded to a non-elastic member while the non-elastomeric member is extended in the machine direction creating a necked material that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes.

"Stretch-bonded" laminate refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-elastic layer is fully extended. Examples of stretch-bonded laminates are disclosed, for example, in U.S. Pat. Nos. 4,720,415, 4,789, 699, 4,781,966, 4,657,802, and 4,655,760, which are incorporated herein by reference in their entirety for all purposes.

"Member" when used in the singular can refer to a single element or a plurality of elements.

Various aspects and embodiments of the invention will be described in the context of a disposable absorbent article, such as a child's training pant. It is, however, readily apparent that the present invention could also be employed with other articles, disposable diapers, feminine care articles, incontinence garments and the like. Typically, the disposable articles are intended for limited use and are not intended to be laundered or otherwise cleaned for reuse. A child's training pant, for example, is discarded after it has become soiled by the wearer. In its various aspects, the invention can provide a distinctive absorbent article which exhibits desirable physical properties, such as softness, flexibility, conformance, trim appearance, reduced gapping and reduced leakage, particularly from around the sides of the article. The article can include an absorbent body structure which exhibits desirable physical properties, such as improved softness, flexibility, durability, conformance and stretchability. As a result, the absorbent structures and articles of the invention can provide increased strength, improved fit, reduced leakage, and reduced clumping, bunching or sagging during use.

With reference to the figures, an article, such as the representatively shown child's training pant 10, includes a body or chassis 20 having a lengthwise, longitudinal direction Y, a lateral, transverse cross-direction X, a front waist region 14, a back waist region 12, and an intermediate crotch region 16 interconnecting the front and back waist regions. The waist regions 12 and 14 comprise those portions of the article 10 which when worn, wholly or partially cover or encircle the waist or mid-lower torso of the wearer. In particular configurations, the front 14 and back 12 waist regions may include elastic front and back waistband portions 17, 11. In the illustrated embodiments, the elastic waistband portions 11,17 are generally continuous around the waist opening 24 of the article. In an alternate embodiment, the waistband portions 11,17 may extend only partially across their respective waist regions. The intermediate crotch region 16 lies between and interconnects the waist regions 14 and 12, and comprises that portion of the article 10 which, when worn, is positioned between the legs of the wearer and covers the lower torso of the wearer. Thus, the intermediate crotch region 16 is an area where repeated fluid surges typically occur in the training pant or other disposable absorbent article when the wearer is in an upright position.

Figure 2:
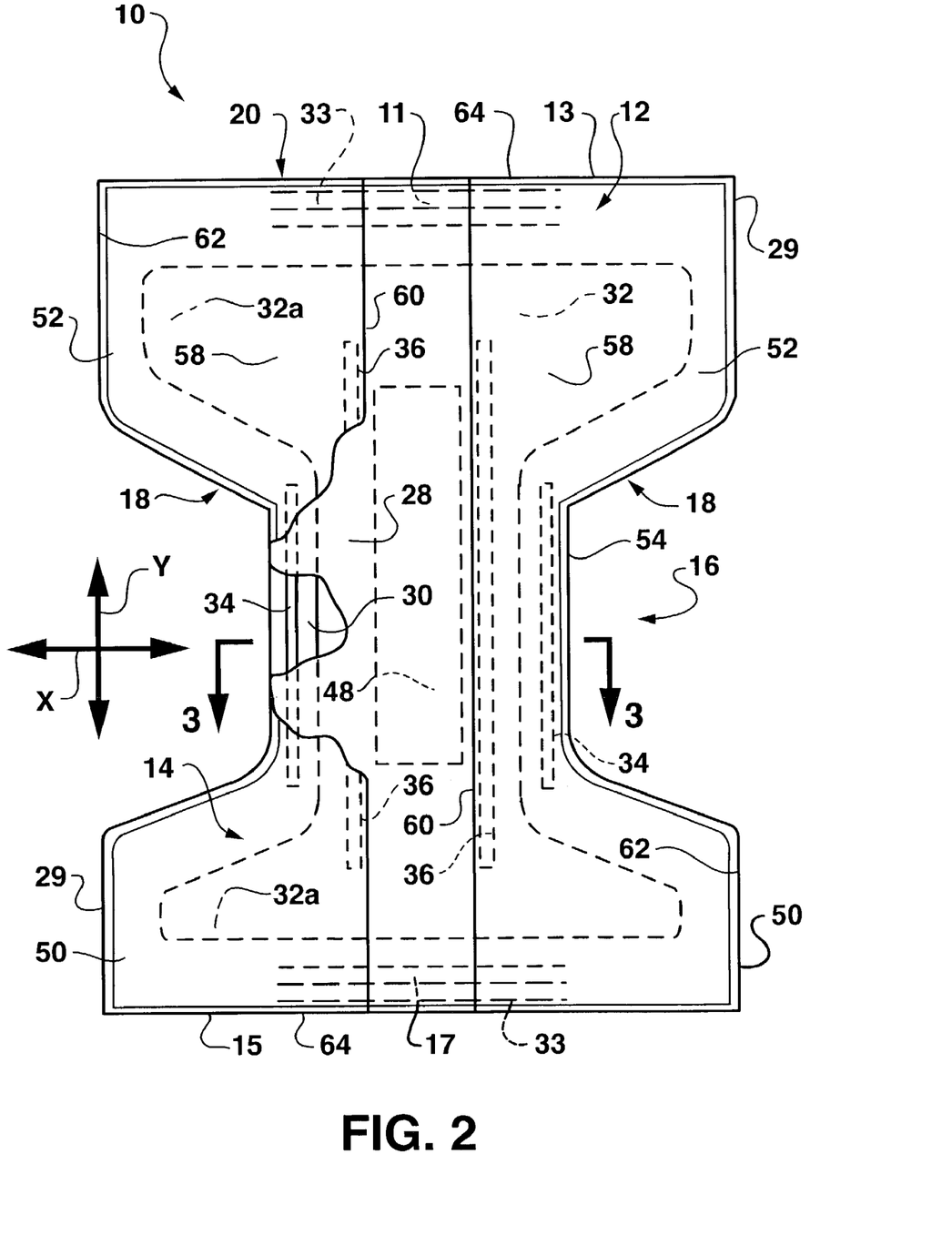
FIG. 2 is a simplified bodyside plan view of an absorbent article chassis with all elastic components being in a tensioned state.
Figure 3:
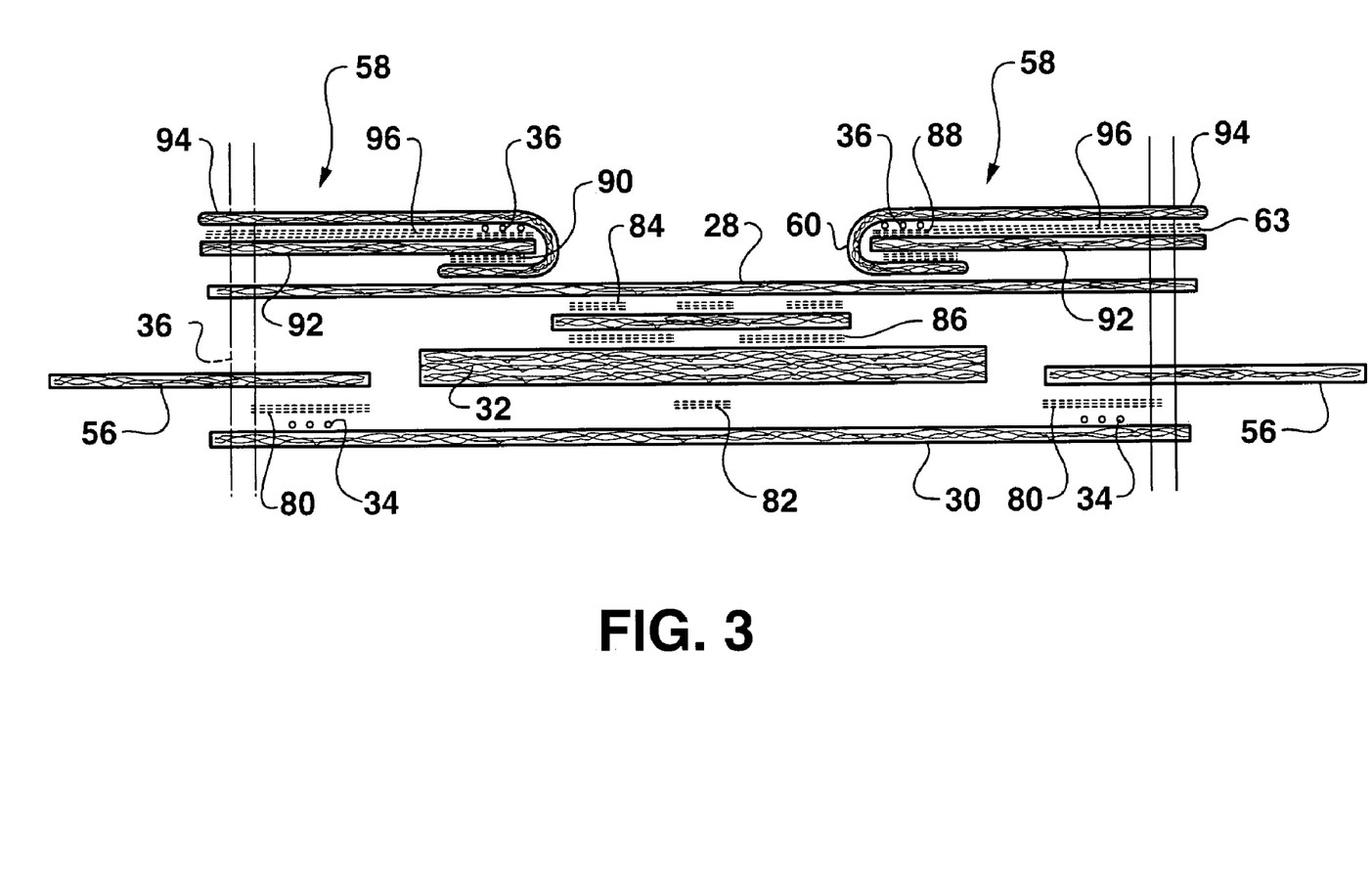
FIG. 3 is a schematic cross-sectional view of the chassis taken along the lines indicated in FIG. 2.

The article 10 includes a substantially liquid-impermeable outer cover member 30, a liquid-permeable bodyside liner 28, and an absorbent body structure 32 sandwiched between the outer cover member 30 and the bodyside liner layer 28. The absorbent body structure may be secured to the outer cover member 30 by an adhesive 82, and secured to the bodyside liner 28 by an adhesive 84, as represented in FIG. 3. In certain embodiments, a surge layer 48 may be optionally located adjacent the absorbent structure and attached by way of adhesive 86 (FIGS. 2 and 3). In certain configurations, the outer cover member 30 and absorbent body structure 32 may be stretchable, particularly in the lateral or transverse direction X. For example, the outer cover member 30 may be made substantially of an elastomeric material, and the absorbent body structure may include an elastomeric absorbent material. In certain embodiments, the bodyside liner 28 is also stretchable. For example, the bodyside liner 28 may be made of an elastomeric material.

In the illustrated embodiment of the article 10, as shown in FIG. 2, the chassis 20 includes laterally extending front ear portions 50 and back ear portions 52. In the illustrated embodiment, the ear portions are an extension of the chassis structure and may be, for example, extensions of the outer cover member 30, bodyside liner 28, or both. This configuration may be desirable particularly if the chassis 20, is stretchable in the transverse direction X, particularly across the front and back waist regions 14,12. For example, the chassis may include an elastomeric cover member 30, elastomeric bodyside liner 28, and any combination of other elastomeric components that in combination render a stretchable unitary chassis.

Figure 1:
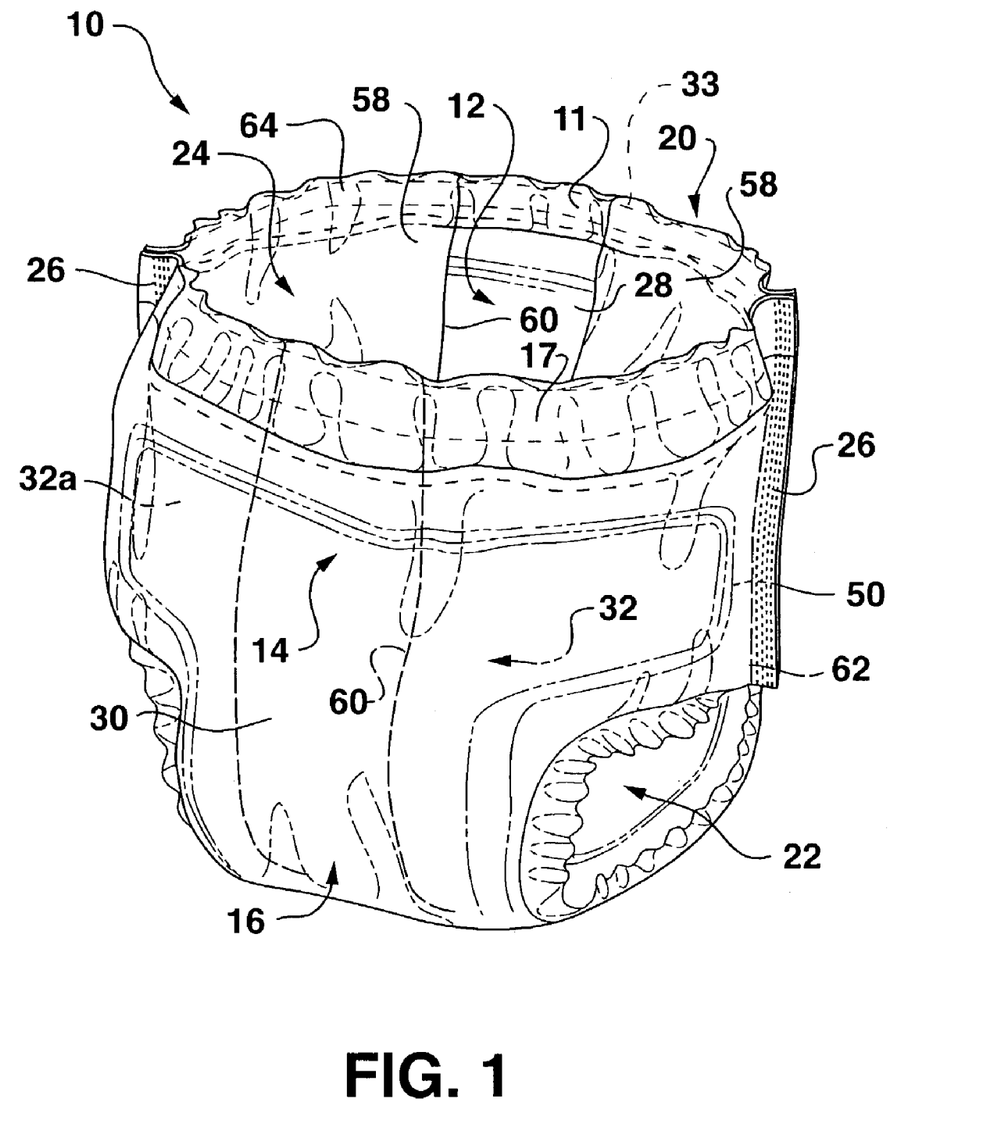
FIG. 1 is a perspective view of an embodiment of an absorbent article, in this case a child's training pant, in accordance with the invention.

The absorbent body structure 32 includes laterally extending wing portions 32a, as seen in phantom lines in FIGS. 1 and 2. The wing portions extend at least partially into the ear portions 50, 52. In a desirable embodiment, the wing portions 32a extend to adjacent the side seams 26 and thus the absorbent body structure 32 generally encircles the waist region of a wearer.

The training pant 10 may be of a style and configuration wherein the front and back ear portions 50, 52 have lateral sides 29 that are brought together upon folding the chassis to form a pant structure having the waist opening 24 and leg openings 22. The lateral sides 29 cooperate with the lateral sides of the crotch region 16 of the chassis 20 to define curved leg contours 18, as particularly seen in FIG. 2. The curved leg contours 18 define the leg openings 22 when the article is assembled. The lateral sides 29 are bonded in a known manner so as to define side seams 26 of the pant structure. With this type of configuration, the pant 10 is pulled on by the wearer in a manner similar to underwear. Desirably, these seams 26 may be separable or tearable so that the pant 10 may be removed from the wearer by tearing the seams 26 and removing the article in a manner similar to a diaper. In an alternate embodiment, the front and back ear portions 50, 52 may be separable and re-attachable at the side seams 26. A fastening system, such as a hook-and-loop system, may be used to interconnect the first waist region 12 with the second waist region 14 to define the pant structure and hold the article on a wearer. Additional suitable releasable fastening systems are described in U.S. Pat. No. 6,231,557 B1 and the International Application WO 00/35395, these references being incorporated herein by reference in their entirety for all purposes.

The article 10 also incorporates longitudinally extending leak guards 58 (also known as "containment flaps" in the art) disposed over the bodyside liner 28. The guards 58 have longitudinal ends 64 that are attached to the chassis 20 generally at longitudinal ends 13, 15 thereof. For example, the guards 58 may extend over and be attached to the waist band portions 11, 17, for example by sonic bonding. The guards 58 have an outboard lateral side 62 that is attached to the chassis desirably outboard of the underlying absorbent body structure 32. The outboard sides 62 have a shape and contour corresponding generally to that of the front and back ear portions 50, 52 such that the guards 58 extend laterally beyond the wing portions 32a of the absorbent body structure. For example, the laterally outboard sides 62 may be generally coextensive with the lateral sides 29 of the chassis 20 and be bonded with the side seams 26. Referring to FIG. 3, the lateral outboard sides 62 may be attached along the crotch region 16 and contoured sides of the ear portions 50, 52 by way of, for example, a generally continuous sonic bond line 63. The guards 58 have a laterally inboard "free" side 60 that extends above and over the underlying absorbent body structure 32 such that the guards essentially define a containment pocket along the lateral sides of the absorbent structure 32.

A wide range of materials are suitable for use as the leak guards 58. For example, the guards 58 may be a nonwoven material such as a spunbond, meltblown, spunlaced, or carded polymeric material, a film material such as a polyolefin or polyurethane film, a foam material, or combinations thereof. The guards may also include materials described herein as being suitable for the outer cover member 30 or liner 28. The guards 58 may be substantially liquid impermeable, may be permeable to only gas, or may be permeable to both gas and liquid. It is generally desired that the guards 58 be formed from a material which is substantially impermeable to liquids, and which provides a cloth-like feel to the wearer. For example, the guards may contain a non-woven/liquid impervious film laminate construction. The guards may be formed of a woven or non-woven web which has been totally or partially treated to impart a desired level of liquid impermeability, or wettability and hydrophilicity.

It is also generally desirable that the outer or body facing surface of the guards 58 be at least partially wettable or hydrophilic to at least partially absorb any body exudates which become trapped between the guards and the wearer.

In embodiments wherein the guards 58 are formed of a generally non-elastomeric material, provision is made to ensure that the guards are stretchable with the portions of the chassis 20 to which they are attached. For example, the longitudinal ends of the guards 58 may be gathered where attached to the elastic waistband portions 11, 17 so as to stretch therewith.

As discussed, the leak guards 58 may desirably be formed substantially of an elastomeric material or elastomeric composite material so as to be stretchable in the transverse direction. In this manner, regardless of the points of attachment of the guards laterally or at their respective longitudinal ends, the guards will not detract from the desired stretchable characteristics of another component of the article. The leak guards 58 are not limited to any particular type of elastomeric material, so long as such material is moisture resistant and preferably presents a cloth-like feel to the wearer. Suitable materials may be, for example, a neck-bonded laminate, stretch-bonded laminate, stretch-thermal laminate, or any combination of materials that provides moisture resistance and a desired degree of cloth-like feel to the wearer. A particularly suitable material is a neck-bonded laminate (NBL) of an elastic polyethylene film and neck stretched spunbond polypropylene. As represented in FIG. 3, the guards 58, may be a laminate composite of a liquid impervious elastic film 92 and the necked spunbond web 94. An adhesive 96 is used to laminate the materials together; alternatively or in addition, sonic bonds/welding can be used to laminate the materials. Elastic strands 36 may be incorporated into the laminating process with an adhesive 88 to produce the type of structure shown in FIG. 3. An extension or "flap" (not separately illustrated) of the necked spunbond web 94 may be folded over along the free side 60 of the guards 58 and attached to the underside of the elastic film 92 with an adhesive 90. It should be appreciated, however, that the invention is not limited to this structural configuration of leak guards 58. Suitable other constructions and arrangements for the leak guards 58 are generally known to those skilled in the art and examples are also described in U.S. Pat. No. 4,704,116, incorporated herein in its entirety for all purposes.

FIG. 2 shows a plan view of the representative training pant 10 in its generally flat-out, uncontracted state (i.e., with substantially all elastic induced gathering and contraction removed). In this view, the bodyside surface of the pant 10 which contacts the wearer is facing the viewer, and portions of the structure are partially cut away to more clearly show the interior construction of the article. The outer edges of the article 10 define a periphery with longitudinally extending lateral sides and laterally extending ends 13,15. The longitudinal ends 13, 15 are shown as straight, but optionally, may be curvilinear. The lateral sides are defined by the lateral sides 29 of the front and back ear portions 50, 52, and lateral sides 54 of the crotch region 16. Laterally inwardly extending curved leg contours 18 are defined generally between the front and back ear portions and extend longitudinally generally along the crotch region 16. As mentioned, when the pant structure is formed by joining the lateral sides 29 of the front and back ear portions 50, 52, these contours 18 define leg openings for the article 10.

Elastomeric gathering members, such as leg elastics 34 and waist elastics 33 may be provided, as is well known in the art. The liner 28, outer cover 30, absorbent structure 32, surge layer 48, and elastic members 34 and 36 may be assembled together into a variety of well-known absorbent article configurations.

The leg elastic members 34 may be located in the lateral side margins of the chassis 20, particularly along the lateral sides of the crotch region 16, and are configured to draw and hold the chassis 20 against the legs of the wearer. The elastic members 34 are secured to the chassis 20, for example with an adhesive 80, in an elastically contracted state so that in a normal under-strain condition, the elastic members 34 effectively contract against the chassis. The use of elastic leg members in absorbent articles such as disposable diapers and training pants is widely known and understood in the art.

The use of elastic waistbands is also widely known and used in the art. In the illustrated embodiment of FIG. 1, the waist elastics 33 are provided generally across the entirety of the front and back waistbands 11, 17. In alternate embodiments, the waist elastics 33 may extend only partially across the front and back waistbands, as represented in FIG. 2. The waist elastics 33 may be composed of any suitable elastomeric material, such as an elastomeric film, an elastic foam, multiple elastic strands, an elastomeric fabric, and the like. Embodiments of waistband structures that may be utilized with articles 10 according to the invention are also described in U.S. Pat. Nos. 5,601,547; 6,358,350 B1; 6,336,921 B1; and 5,711,832, incorporated by reference in their entirety for all purposes.

The liner 28 and outer cover member 30 may be generally coextensive, and may have length and width dimensions which are generally larger than and extend beyond the corresponding dimensions of the absorbent structure 32. The extending portions define the corresponding side and end margins that allow for the waistbands 11,17, leg elastics 34, and side seams 26 used to attach together the outer cover member 30, liner 28, and leak guards 58. Optionally, the bodyside liner 28 and outer cover member 30 may not be coextensive. The outer cover member 30 may be composed of a liquid permeable material, but desirably comprises a material which is configured to be substantially impermeable to liquids. For example, a typical outer cover can be manufactured from a thin plastic film, a composite laminate, or other flexible, substantially liquid-impermeable material. As used in the present specification, the term "flexible" refers to materials which are compliant and which will readily conform to the general shape and contours of the wearer's body.

Alternative constructions of the outer cover member 30 may comprise a woven or non-woven fibrous web layer which has been totally or partially constructed or treated to impart the desired levels of liquid impermeability to selected regions that are adjacent or proximate the absorbent body. For example, the outer cover may include a gas-permeable, nonwoven fabric layer laminated to a polymer film layer which may or may not be gas-permeable. Other examples of fibrous, cloth-like outer cover materials can comprise a stretch thinned or stretch thermal laminate material. Although the outer cover 30 typically provides the outermost layer of the article, optionally the article may include a separate outer cover component member which is additional to the outer cover member.

In a particular embodiment, the outer cover 30 may be formed substantially from an elastomeric material and is thus stretchable. In this embodiment, the outer cover 30 may define the entire front and back waist regions 14,12, including the front and back ear portions 50, 52. The outer cover 30 may, for example, be composed of a single layer, multiple layers, laminates, spunbond fabrics, films, meltblown fabrics, elastic netting, microporous web, bonded carded webs or foams comprised of elastomeric or polymeric materials. Elastomeric nonwoven laminate webs may include a nonwoven material joined to one or more gatherable nonwoven webs, films, or foams. Stretch Bonded Laminates (SBL) and Neck Bonded Laminates (NBL) are examples of elastomeric composites. Nonwoven fabrics are any web of material which has been formed without the use of textile weaving processes which produce a structure of individual fibers which are interwoven in an identifiable repeating manner. Examples of suitable materials are Spunbond-Meltblown fabrics, Spunbond-Meltblown-Spunbond fabrics, Spunbond fabrics, or laminates of such fabrics with films, foams, or other nonwoven webs. Elastomeric materials may include cast or blown films, foams, or meltblown fabrics composed of polyethylene, polypropylene, or polyolefin copolymers, as well as combinations thereof. The elastomeric materials may include PEBAX® elastomer (available from AtoChem located in Philadelphia, Pa.), HYTREL® elastomeric polyester (available from E. I. DuPont de Nemours located in Wilmington, Del.), KRATON™ elastomer (available from Shell Chemical Company located in Houston, Tex.), or strands of LYCRA® elastomer (available from E. I. DuPont de Nemours located in Wilmington, Del.), or the like, as well as combinations thereof. The outer cover 30 may include materials that have elastomeric properties through a mechanical process, printing process, heating process, or chemical treatment. For examples such materials may be apertured, creped, neck-stretched, heat activated, embossed, and micro-strained; and may be in the form of films, webs, and laminates.

The bodyside liner 28 presents a body-facing surface which is compliant, soft-feeling, and non-irritating to the wearer's skin. Further, the bodyside liner 28 can be less' hydrophilic than the absorbent body 32, and is sufficiently porous to be liquid permeable, permitting liquid to readily penetrate through its thickness to reach the absorbent body. A suitable bodyside liner layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner layer 28 is typically employed to help isolate the wearer's skin from liquids held in absorbent body 32.

Various woven and nonwoven fabrics can be used for bodyside liner 28. For example, the bodyside liner may include a meltblown web, a spunbonded web, or a bonded-carded-web composed of the desired fibers. The various fabrics can be composed of natural fibers, synthetic fibers or combinations thereof. In particular aspects, the bodyside liner 28 may be comprised of polymer fibers, networks, laminates, liquid permeable films, cellulosic fibers, rayon, water swellable gels, and elastomeric materials, as well as combinations thereof. Suitable materials for the bodyside liner can include meltblown webs, airlaid webs, spunbond webs, or bonded-carded webs of synthetic continuous or discrete polymer fibers and/ or natural fibers, a pattern bonded spunbonded web, airlaid web, or bonded carded web, as well as combinations thereof. Suitable polymers can include, polypropylene, polyethylene, polyester, and bicomponent materials composed of these polyolefins.

The bodyside liner fabrics may be composed of a substantially hydrophobic material, and the hydrophobic material may optionally be treated with a surfactant or otherwise processed to impart a desired level of wettability and hydrophilicity. In a particular embodiment of the invention, the bodyside liner 28 can be a nonwoven, spunbond polypropylene fabric which is necked approximately 60%. Strands of KRATON G2760 elastomer material may be adhered to the necked spunbond material. The fabric can be surface treated with an operative amount of surfactant, such as about 0.45% AHCOVEL Base N62 surfactant, available from Uniqema, a division of ICI, a business having offices located in New Castle, Del. The surfactant can be applied by any conventional means, such as spraying, printing, brush coating or the like.

In particular embodiments wherein it is desired that the bodyside liner layer 28 be stretchable, suitable elastomeric materials can include elastic strands, LYCRA® elastics, elastic films, cast or blown; nonwoven elastic webs, meltblown or spunbond elastomeric fibrous webs, as well as combinations thereof. Examples of elastomeric materials include KRATON® elastomers, HYTREL® elastomers, ESTANE® elastomeric polyurethanes (available from B. F. Goodrich and Company located in Cleveland, Ohio), or PEBAX® elastomers. The bodyside liner may include blends or laminates of fibers, scrim, webs, and films with perforations, apertures, creping, heat activation, embossing, micro-straining, chemically treatment, or the like, as well as combinations thereof.

The bodyside liner 28 and outer cover 30 are connected or otherwise associated together in an operable manner. As used herein, the term "associated" encompasses configurations in which the bodyside liner 28 is directly joined to the outer cover 30 by affixing the bodyside liner 28 directly to the outer cover 30, and configurations wherein the bodyside liner 28 is indirectly joined to the outer cover 30 by affixing the bodyside liner 28 to intermediate members which in turn are affixed to the outer cover 30. The bodyside liner 28 and outer cover 30 can, for example, be joined to each other in at least a portion of the training pant periphery by suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the bodyside liner 28 to the outer cover 30. It should be readily appreciated that the above-described attachment means may also be employed to suitably interconnect, assemble and/or affix together the various other component parts of the articles which are described herein.

The absorbent body structure 32 (including wing portions 32a and optional surge layer 48) is positioned between the outer cover 30 and the bodyside liner 28. The absorbent body structure 32 can be any structure or combination of components which are generally compressible, conformable, non-irritating to a wearer's skin, and capable of absorbing and retaining liquids and certain body wastes. For example, the structure 32 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from U.S. Alliance of Childersburg, Ala., USA, and is a bleached, highly absorbent sulfate wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

As a general rule, the superabsorbent material is present in the absorbent web in an amount of from about 0 to about 90 weight percent based on total weight of the web. The web may have a density within the range of about 0.10 to about 0.35 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a suberabsorbent material is capable of absorbing at least about 15 times its weight in liquid, and desirably is capable of absorbing more than about 25 times its weight in liquid. Suitable superabsorbent materials are readily available from various suppliers. For example, Favor 888 superabsorbent is available from Stockhausen GmbH of Germany; and Drytech 2035 is available from Dow Chemical Company, of Midland Mich., USA.

After being formed or cut into a desired shape, the absorbent web material may be wrapped or encompassed by a suitable tissue wrap that aids in maintaining the integrity and shape of the absorbent structure 32.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. Nos. 4,100,324 to *Anderson, et al.*; 5,284,703 to

*Everhart, et al.*; and 5,350,624 to *Georger, et al.*; which are incorporated herein in their entirety by reference thereto for all purposes.

With particular embodiments of an absorbent article according to the invention, it may be desired that the absorbent body structure 32 is elastomeric. For example, in the embodiment as shown in FIG. 1 wherein generally the entire chassis 20 is stretchable or elastomeric, it may be desired that the absorbent body structure 32 is also stretchable so as not to inhibit the stretchability of other components. For this purpose, the absorbent web material can include elastomeric fibers in an amount which is at least a minimum of about 2 wt %. The amount of elastomeric fibers can alternatively be at least about 3 wt %, and can optionally be at least about 5 wt % to provide improved performance. In addition, the amount of elastomeric fibers can be not more than about 60 wt %. Alternatively, the amount of elastomeric fibers can be not more than about 45 wt %, and optionally, can be not more than about 30 wt % to provide improved benefits. These values are important because they can provide the absorbent retention portion with desired levels of stretchability and structural stability without excessively degrading the physical properties or the liquid-management properties of the absorbent structure. An absorbent web material with an excessively low proportion of elastomeric fibers may be insufficiently stretchable, and a web material with an excessively high proportion of elastomeric fibers may exhibit an excessive degradation of its absorbency functionalities, such as poor intake, poor distribution, poor retention of liquid and/or an excessive tension force when stretched.

The absorbent body structure 32—may include an elastomeric coform absorbent web material. In particular aspects, the elastomeric coform material can have an overall coform basis weight which is at least a minimum of about 50 g/m$^2$. The coform basis weight can alternatively be at least about 100 g/m$^2$ and can optionally be at least about 200 g/m$^2$ to provide improved performance. In addition, the coform basis weight can be not more than about 1200 g$^2$. Alternatively, the coform basis weight can be not more than about 900 g/m$^2$, and optionally, can be not more than about 800 g/m$^2$ to provide improved benefits. These values are important because they can provide the absorbent body structure with desired stretchability and structural stability without excessively degrading the physical properties or the liquid-management functionalities of the absorbent body structure. Retention portions having excessively low proportions of elastomeric coform material may not be sufficiently stretchable. An absorbent web material having excessively large amounts of elastomeric coform materials can exhibit an excessive degradation of their absorbency functionalities, such as an excessive degradation of intake, distribution and/or retention properties.

Other examples of elastomeric absorbent structures are described in U.S. Pat. No. 6,362,389 B1, incorporated herein by reference for all purposes.

The absorbent web material utilized in the absorbent body structure 32 is also selected so that the individual absorbent body structure possesses a particular individual total absorbency depending on the intended article of use. For example, for infant care products, the total absorbency can be within the range of about 300-900 grams of 0.9 wt % saline, and can typically be about 500 g of saline. For adult care products, the total absorbency can be within the range of about 1000-1600 grams of saline, and can typically be about 1300 g of saline. For feminine care products, the total absorbency can be within the range of about 7-50 grams of saline, and can typically be within the range of about 30-40 g of saline.

As mentioned, the absorbent body structure 32 may also include a surge management layer 48 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. The surge layer can be located below the bodyside liner layer 28. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference in their entirety for all purposes.

It should be understood that resort may be had to various other embodiments, modifications, and equivalents to the embodiments of the invention described herein which, after reading the description of the invention herein, may suggest themselves to those skilled in the art without departing from the scope and spirit of the present invention.

What is claimed is:

1. A pant-like absorbent article having a longitudinal direction and longitudinal ends, and a lateral direction and lateral sides, said article comprising:
   a front waist region at a first longitudinal end, a back waist region at an opposite longitudinal end, and a crotch region extending longitudinally between said front and back waist regions;
   laterally extending front and back ear portions defined at opposed lateral sides of said front and back waist regions, said front and back ear portions having laterally outward sides;
   a laterally inwardly directed leg contour defined in each said lateral side between respective said front and back ear portions;
   an absorbent body structure extending longitudinally along said crotch region generally from said front waist region to said back waist region, said absorbent body structure including laterally extending wing portions that extend laterally beyond said crotch region and into said front and back ear portions substantially to said laterally outward sides of said front and back ear portions, said wing portions being capable of absorbing and retaining liquids and certain body wastes;
   wherein upon folding said article about a transverse fold line at a longitudinal mid-point thereof to form a pant structure, said laterally outward sides of said front and back ear portions join at side seams of said article such that said leg contours define respective leg openings and said wing portions of said absorbent body structure in said front and back ear portions generally encircle a wearer's waist; and
   longitudinally extending leak guards, each said guard having a free laterally inward side and a laterally outward side with a contour corresponding generally to that of said leg contours and said laterally outward sides of said front and back ear portions, said leak guards extending to said longitudinal ends of said front and back waist regions from said free laterally inward side to said laterally outward side of said leak guards said laterally outward side of said leak guards attached to said laterally outward sides of said front and back ear portions and along said leg contours laterally outward of said absorbent body structure in said crotch region and said wing portions of said absorbent body structure in said front and back ear portions so as to define a containment pocket along said leg contours and that encompasses said absorbent article from said first longitudinal end to said opposite longitudinal end.

2. The absorbent article as in claim 1, wherein said article is a child's training pant.

3. The absorbent article as in claim 1, wherein at least said front and back ear portions of said front and back waist regions are stretchable in a transverse direction, said leak guards being stretchable so as to stretch with said ear portions.

4. The absorbent article as in claim 3, wherein said front and back ear portions are elastomeric.

5. The absorbent article as in claim 3, wherein said absorbent body structure is generally elastomeric.

6. The absorbent article as in claim 3, wherein said front and back waist portions are generally stretchable in a transverse direction across their entirety.

7. The absorbent article as in claim 6, wherein said leak guards are formed of a generally elastomeric material, longitudinal ends of said leak guards attached to waistbands of said front and back waist portions.

8. The absorbent article as in claim 6, wherein said leak guards are formed of a generally non-elastomeric material, said longitudinal ends of said leak guards attached to waistbands of said front and back waist portions in a gathered state so as to stretch therewith.

9. The absorbent article as in claim 1, comprising an elastomeric outer cover member, and a liquid permeable topsheet member, and an elastomeric absorbent body structure sandwiched between said outer cover member and said topsheet member, said leak guards formed of an elastomeric material so as to stretch with said outer cover member.

10. The absorbent article as in claim 1, wherein said laterally inward sides of said leak guards are elasticized.

11. The absorbent article as in claim 1, wherein said ear portions are bonded at said side seams to define said pant structure.

12. The absorbent article as in claim 11, wherein said side seams are tearable for removing the article from a wearer.

13. The absorbent article as in claim 1, wherein said side seams are releasable and re-attachable.

14. The absorbent article as in claim 1, wherein said absorbent body structure comprises laterally extending wing portions extending laterally along both of said front and back ear portions.

15. An absorbent article, comprising:
a generally elastomeric absorbent chassis comprising a bodyside liner, an outer cover bonded to said bodyside liner, and an absorbent structure disposed between said bodyside liner and said outer cover, said absorbent chassis defining a front waist region, a back waist region, and a crotch region extending between said front and back waist regions;

said front and back waist regions further comprising laterally extending ear portions having laterally outward sides, said ear portions defining leg contours with said crotch region along opposite lateral sides of said chassis;

said absorbent structure further comprising a central longitudinally extending portion and elastomeric wing portions that extend laterally beyond said central longitudinally extending portion and into said front and back ear portions substantially to said laterally outward sides of said front and back ear portions, said wing portions being capable of absorbing and retaining liquids and certain body wastes;

elastomeric leak guards having free laterally inward sides and laterally outward sides attached adjacent to said laterally outward sides of said ear portions, said leak guards extending to longitudinal ends of said front and back waist regions from said free laterally inward side to said laterally outward side of said leak guards such that said leak guards define a containment pocket along said leg contours that encompasses said front and back ear portions and longitudinal ends of said absorbent structure; and wherein upon forming said chassis into a pant structure with said front and back ear portions joined at side seams of said article, said absorbent structure elastomeric wing portions and said leak guards provide leakage protection to a wearer generally completely around the front and back waist regions.

16. The absorbent article as in claim 15, wherein said article is a child's training pant.

17. The absorbent article as in claim 15, wherein said side seams are bonded tearable seams.

18. The absorbent article as in claim 15, wherein said side seams are releasable and re-attachable.

19. The absorbent article as in claim 15, wherein said absorbent structure includes an elastomeric absorbent material along said central portion and said wing portions.

20. The absorbent article as in claim 19, wherein said absorbent structure is attached to said outer cover layer along said central region and said wing portions.

21. The absorbent article as in claim 15, wherein said leak guards are made of an elastomerically stretchable material.

* * * * *